United States Patent [19]

Schmitt

[11] 4,290,695

[45] Sep. 22, 1981

[54] METHOD AND APPARATUS FOR MEASUREMENT OF TRANSMITTANCE AND SCATTER OF LIGHT IN WATER

[75] Inventor: Harold W. Schmitt, Knoxville, Tenn.

[73] Assignee: Environmental Systems Corporation, Knoxville, Tenn.

[21] Appl. No.: 80,056

[22] Filed: Sep. 28, 1979

[51] Int. Cl.³ .......................................... G01N 21/01
[52] U.S. Cl. .................................... 356/73; 356/341; 356/434; 356/442
[58] Field of Search ................ 356/73, 339, 341, 434, 356/438, 439, 442; 250/574, 575

[56] References Cited

U.S. PATENT DOCUMENTS

| 3,652,850 | 3/1972 | Briggs | 356/341 X |
| 4,037,973 | 7/1977 | Carr | 250/575 X |
| 4,125,328 | 11/1978 | Suga | 356/73 |

Primary Examiner—Vincent P. McGraw
Attorney, Agent, or Firm—Luedeka & Fitch

[57] ABSTRACT

Precise quantification of turbidity is obtainable through multiple determinations of the light attenuation coefficient of the particulate-bearing medium at a plurality of path lengths in the attenuating medium, and through multiple determinations of the scattering coefficient of the particulate-bearing medium at a selected angle of incidence and at a plurality of path lengths in the attenuating medium. In the preferred apparatus, these determinations employ a common light source and a common detector. In the present system, there are eliminated such adverse factors as light-source instability, detector instability, variations in particulate deposits on windows, and other problems, through the use of the ratio of the intensity measurements at different locations in the medium.

4 Claims, 8 Drawing Figures

METHOD AND APPARATUS FOR MEASUREMENT OF TRANSMITTANCE AND SCATTER OF LIGHT IN WATER

This invention relates to methods and apparatus for measuring the effects of suspended particulates upon the transmission of light through a liquid medium, at times referred to in the art as turbidimeters.

As one example, the presence of particulates in a natural stream of water affects the degree of penetration of sunlight into the stream hence affects the growth of marine flora and fauna in the stream. In ecological studies, for example, it thus becomes important to know the precise effect of existing particulates upon the passage of light through the medium, either at a given time and over an extended period of time.

Possible particulates suspended in a liquid medium may vary greatly in their nature, such as the soil particulates that are carried into a water stream through erosion wherein the particulates not only vary in size and shape but also vary in their chemical nature. All such particulates, however, exhibit some influence upon a beam of light which is directed into the particulate-containing medium, thereby giving rise to the term "turbidity" which has come to be applied loosely as a measure of the lack of clarity of a liquid medium that contains suspended particulates. This term is less than adequate for such purpose in that it is not susceptible to precise quantification.

In conventional turbidimetry the Jackson Candle Turbidimeter is generally employed. A column of liquid is increased in length until the image of the flame from a "standard" candle viewed through the column loses contrast and becomes diffused. The length of the column at which the image is degraded into a uniform disc of light is read against a scale of units designated Jackson Turbidity Units (JTU). This method has become generally accepted, even though the quantity it measures is not well-defined and is based on the subjective judgment of an observer.

While the Jackson measurement is still in wide use today, most electronic instruments, including laboratory and field monitors, employ designs measuring light scatter perpendicular to the incident beam. Other electronic instruments employ measurements of the attenuation of the incident beam. In general, neither measurement correlates well with JTU values, nor do they correlate well with the amount of particulate matter present. Most especially, the methods themselves are not standardized. Among the problems which have plagued the prior art are light-source instability, detector instability, variations in particulate deposits on sight windows, etc. Further, many of these prior art measurements have attempted to measure light transmission through the medium in exact conventional units of light transmittance, thereby apparently unknowingly failing to take into consideration extraneous factors such as background light, reflected light and/or other similar factors. Nonuniformity of results has been characteristic of such prior art measurements.

More specifically, in conventional turbidimeters where light transmission is measured, it may be said mathematically that there is measured the intensity of light I, transmitted through a fixed path of length l, from a source of light of intensity $I_o$. As a practical matter, however, $I_o$ commonly is neither well known nor is it stable over the period of time during which a measurement takes place. In addition, the measurement of I, is affected by reduction in light intensity by the accumulation of particulates on the light source, detector, and/or on windows which protect them, and also by variations in detector response or source strength. Consequently, such measurements are both inaccurate and imprecise.

In accordance with the present disclosure, the inventor has found that precise quantification of turbidity is obtainable through multiple determinations of the light attenuation coefficient of the particulate-bearing medium at a plurality of path lengths in the attenuating medium, and through multiple determinations of the scattering coefficient of the particulate-bearing medium at a selected angle of incidence and at a plurality of path lengths in the attenuating medium. In the preferred apparatus, these determinations employ a common light source and a common detector. In the present system, there are eliminated such adverse factors as light-source instability, detector instability, variations in particulate deposits on windows, and other problems, through the use of the ratio of the intensity measurements at different locations in the medium.

It is therefore an object of the present invention to provide an improved method for measuring the effect of particulates in a liquid medium upon the transmission of light through such medium. It is another object to provide a method for substantially simultaneously measuring the transmittance and scatter of light in a liquid medium. It is another object to provide apparatus for measuring transmittance and/or scatter of light in a liquid medium.

Other objects and advantages will be recognized from the following description including the claims and drawings in which:

Figure 1:
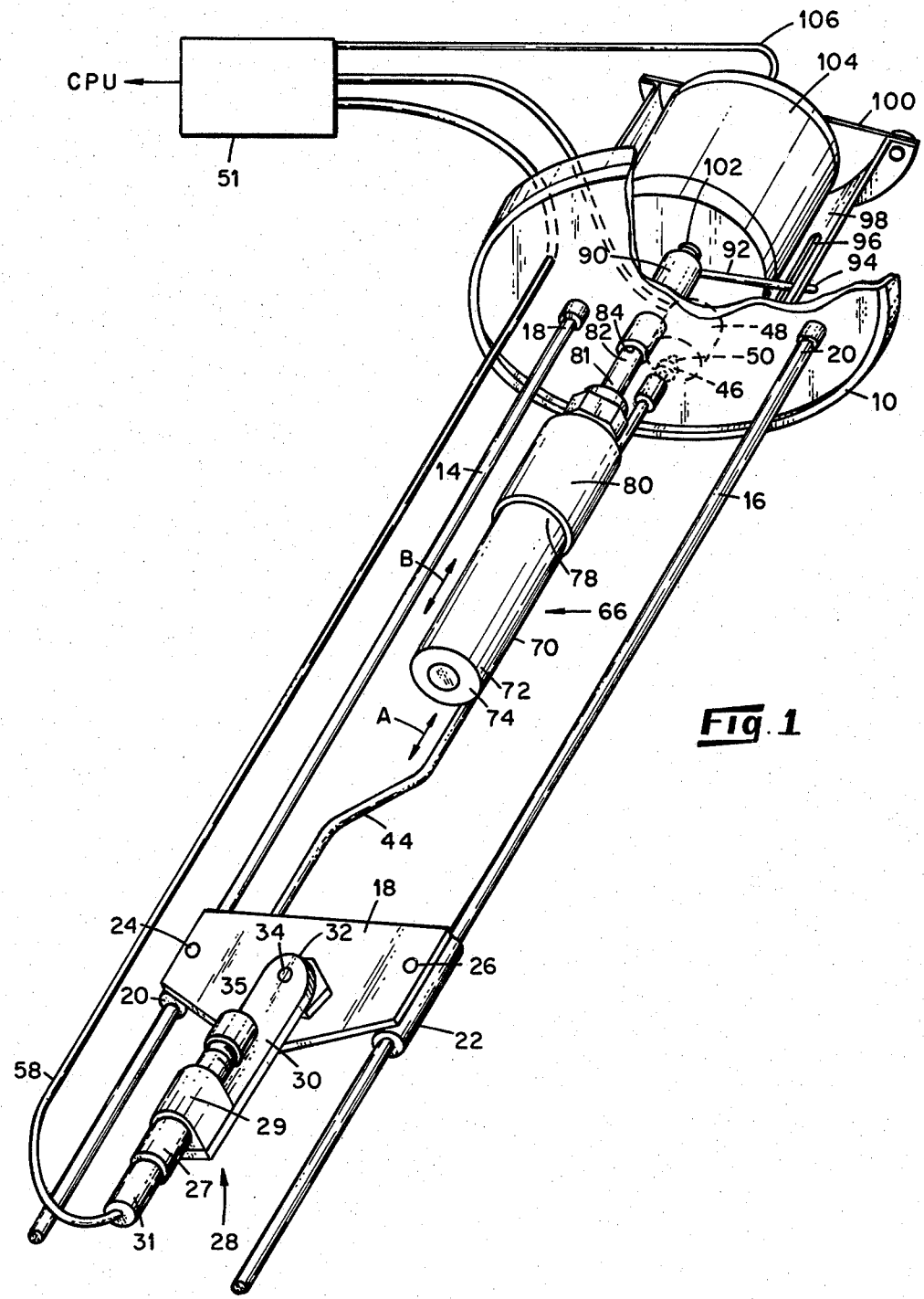
FIG. 1 is a representation of an instrument for measuring transmittance and scatter of light in a liquid medium and embodying various features of the invention.

Generally stated, in a sample volume of a particulate-bearing liquid medium, the penetration of the medium by a light beam of an intensity $I_o$ at the surface of the liquid is influenced by several mechanisms. In most cases, the effects of particulate matter in the medium dominate. The present inventor has determined that quantification of such dominating mechanism is possible through a plurality of determinations of the light attenuation coefficient $\alpha$ of the sample and, preferably, a like plurality of determinations of the scattering coefficient of the sample, both such types of determinations being made at a plurality of path lengths, $l_1$, and $l_2$, within the sample and over a relatively short period of time, e.g., less than one minute, for a given series of determinations.

For short distances, the amount of light lost along the direction of a beam of light in a liquid medium by scattering and absorption is simply proportional to the incident intensity and to the amount of liquid in the light path; that is, the decrease in intensity is proportional to the length of the light path. Thus, referring to FIG. 4:

$$I_b - I_a = I_a \alpha (x_b - x_a) \quad \text{Eq. (1)}$$

or $$\Delta I = -I \alpha \Delta x \quad \text{Eq. (2)}$$

Where $I_a$ and $I_b$ are the intensities at distances $x_a$ and $x_b$, respectively; and $\alpha$ is the proportionality constant giving the fraction of light lost per unit distance along the light path, that is, the light attenuation coefficient. Equation (2) follows from Eq. (1); here $\Delta I$ is the small change in intensity corresponding to the small distance $\Delta x$. The negative sign in Eq. (2) is necessary because I decreases as x increases, that is, $(I_b - I_a)$ is a negative quantity when $(x_b - x_a)$ is a positive quantity.

Writing Eq. (2) in differential form, and integrating from $x=0$, where $I=I_o$, to $x=l_1$, where $I=I_1$, provides the following:

$$I = I \int_o^{I_1} \frac{dI}{I} = x = \int_o^{l_1} -\alpha dx \quad \text{Eq. (3)}$$

then $$\ln \frac{I_1}{I_o} = -\alpha l_1 \quad \text{Eq. (4)}$$

and $$I_1 = I_o e^{-\alpha l_1} \quad \text{Eq. (5)}$$

Equation (5) characterizes the transmission of any radiation through an absorbing and/or scattering medium.

As disclosed herein, the light attenuation coefficient $\alpha$, is one quantity measured. This coefficient is characteristic of the light-attenuating medium, i.e., liquid plus suspended particulates, and is the fraction of light lost per unit distance along the path. (Light loss described by may occur by absorption, scattering, or any combination of mechanism.) Notably, the coefficient $\alpha$ does not depend mathematically on the intensity of the light source, path length through the liquid, etc.

As stated above, the light attenuation coefficient $\alpha$ and its value is the fractional light intensity lost per unit path length in the liquid. Its units might be cm-1, m-1, or percent per centimeter, percent per meter, etc.

As noted, the coefficient of attenuation $\alpha$ describes light attenuation or loss, regardless of the mechanisms by which the light is lost. The mechanisms by which light may be lost or attenuated include absorption by the liquid itself, absorption by particulates in the liquid, scattering by molecules of the liquid and scattering by particulates in the liquid, where the scattering angle is outside the acceptance angle of the detector, and scattering and absorption which may occur at liquid-liquid interfaces when chemically separated liquids co-exist in a sample. As a practical matter, the effects of absorption and scattering by particulates are important in natural water bodies, and also in industrial waste water discharges.

Even where particulate absorption and scattering dominate, $\alpha$ is not expected necessarily to correlate directly with the amount of particulate matter present. The attenuation coefficient $\alpha$ is determined not only by the amount of particulate matter present but also by its size, distribution, and its index of refraction. A consequence of this, for example, is that two liquid samples containing the same concentrations of particulate matter may have different values of $\alpha$, by virtue of different particle size distributions and/or different particle compositions (e.g., indices of refraction).

In accordance with the disclosed method, there is made a measurement of light intensity at two different path lengths $l_1$ and $l_2$ in the attenuating medium. In practice, this means only that the source or detector must be movable and that the distance moved must be measured or known from preset conditions.

Figure 5:
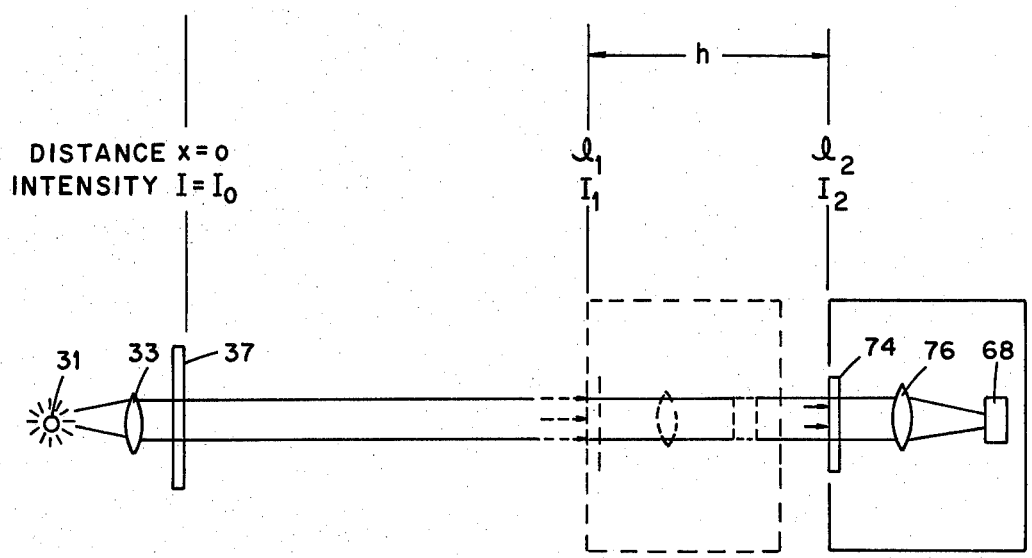
FIG. 5 is a schematic depicting one embodiment of multiple-path-length detection of transmittance of light employing a common light source and a common detector.

To understand this measurement in terms of the mathematics set forth above, reference is directed to FIG. 5 and rewriting of Eq. (5) for each of the distances $l_1$ and $l_2$.

$$I_1 = I_o e^{-\alpha l_1} \quad \text{Eq. (6)}$$

$$I_2 = I_o e^{-\alpha l_2} \quad \text{Eq. (7)}$$

Dividing Eq. (7) by Eq. (6):

$$I_2/I_1 = e^{-\alpha(l_2 - l_1)} \quad \text{Eq. (8)}$$

or $$I_2/I_1 = e^{-\alpha h} \quad \text{Eq. (9)}$$

where $h = l_2 - l_1$, the change in path length.

Equation (9) is the basic equation of the present attenuation measurement. The quantity measured is $\alpha$. To determine $\alpha$ uniquely and unambiguously, it is required only to measure $I_1$ and $I_2$ and to know the distance between the points at which these measurements are made. Once $\alpha$ has been determined, Equation (9) may be solved to obtain the percent of light transmitted $(I_2/I_1)$ over path length h. This proposed method is simple in principle and in practice. It is more precise and more accurate than conventional fixed-distance attenuation measurements, and the quantity measured, $\alpha$, is well-defined and can be understood in physical terms.

The method avoids conventional problems associated with light source and detector stability, fouling of windows, etc.; requiring stability only for a fraction of a minute.

Figure 6:
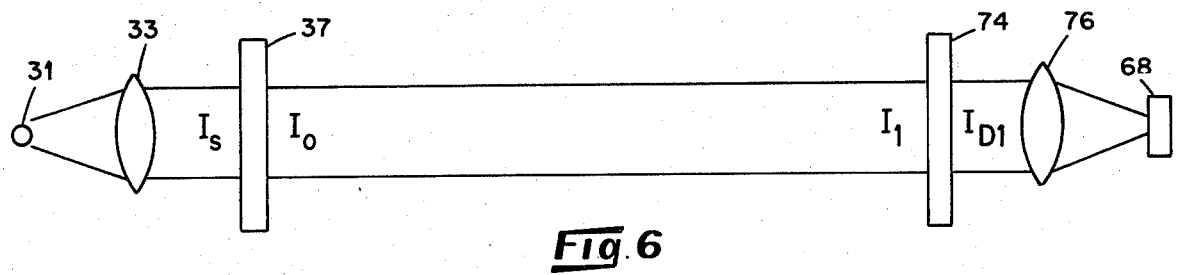
FIG. 6 is a schematic illustrative of certain concepts relating to the effects of window coatings on the measurement of transmittance or scatter of light in a liquid medium.

Commonly, over a period of time, particulate matter will deposit onto the windows protecting various elements such as the source and detector elements of an instrument employed in making light intensity determinations. To understand the effect of these window coatings on the measurement, reference is invited to FIG. 6, which shows that the light intensity incident on the first window is $I_s$, the intensity exiting from the first window is $I_o$ (the incident light intensity $I_o$ referred to above), $I_1$ is the intensity of light transmitted through the liquid and incident on the second window (the same as $I_1$ above), and $I_{D1}$ is the intensity of the light exiting from the second window and incident on the detector at the first location. Defining $w_1$ as the fraction of light lost in the first window and its coatings, and $w_2$ as the fraction of light lost in the second window and its coatings, enables the intensities to be related as follows:

$$I_o = I_s(1-w_1) \quad I_{D1} = I_1(1-w_2) \qquad \text{Eq. (10)}$$

Now since, from Eq. (6), $I_1 = I_o e^{-\alpha l_1}$, combining further produces:

$$I_{D1} + I_s(1-w_1)(1-w_2)e^{-\alpha l_1} \qquad \text{Eq. (11)}$$

The measurement of $\alpha$ as proposed above consists of a measurement at two positions, which in the present invention are actually measured $I_{D1}$ and $I_{D2}$. Rewriting Eq. (11) for position 1 and position 2, and again dividing provides:

$$\frac{I_{D2}}{I_{D1}} = \frac{I_s(1-w_1)(1-w_2)e^{-\alpha l_2}}{I_s(1-w_1)(1-w_2)e^{-\alpha l_1}} \qquad \text{Eq. (12)}$$
$$= e^{-\alpha(l_2-l_1)} \qquad \text{Eq. (13)}$$
$$= e^{-\alpha h} \qquad \text{Eq. (14)}$$

Thus it is seen in this derivation that the window effects, as well as source and detector stability, cancel completely in the ratio measurement. It is important only that $I_s$, $w_1$, $w_2$ and the detector response remain substantially constant for the measurements at positions one and two.

Whereas the light attenuation coefficient value includes certain effects of light scattering, much of the light moving through the medium is by way of scattering, in directions nonaligned, i.e., nonaxial, with the path of the light beam which is the path along which the attenuation coefficient is measured. Thus, in the present invention, there is also measured the incident light which is scattered by various mechanisms, predominately of which are the particulate effects. As disclosed herein, the present inventor has found that such scattering is determinable substantially simultaneously with determination of the attenuation coefficient by measuring the scattering coefficient of the sample.

The scattering coefficient has been found to be characteristic of the sample, i.e., liquid-particulate mixture. Again here, as with $\alpha$, particulate effects dominate; that is, greater particulate concentrations will give rise to larger values of $\sigma$.

The significance of $\sigma$ is that it quantifies the fraction (or percentage) of incident light which is scattered per unit volume of sample and per unit solid acceptance angle of the detector $\Omega$. If the scattering angle is specified (e.g. 90°), and if permissible ranges of v and $\Omega$ are specified, the quantity $\sigma$ has been found to be characteristic of the sample and independent of any specific instrumental unit.

Figure 7:
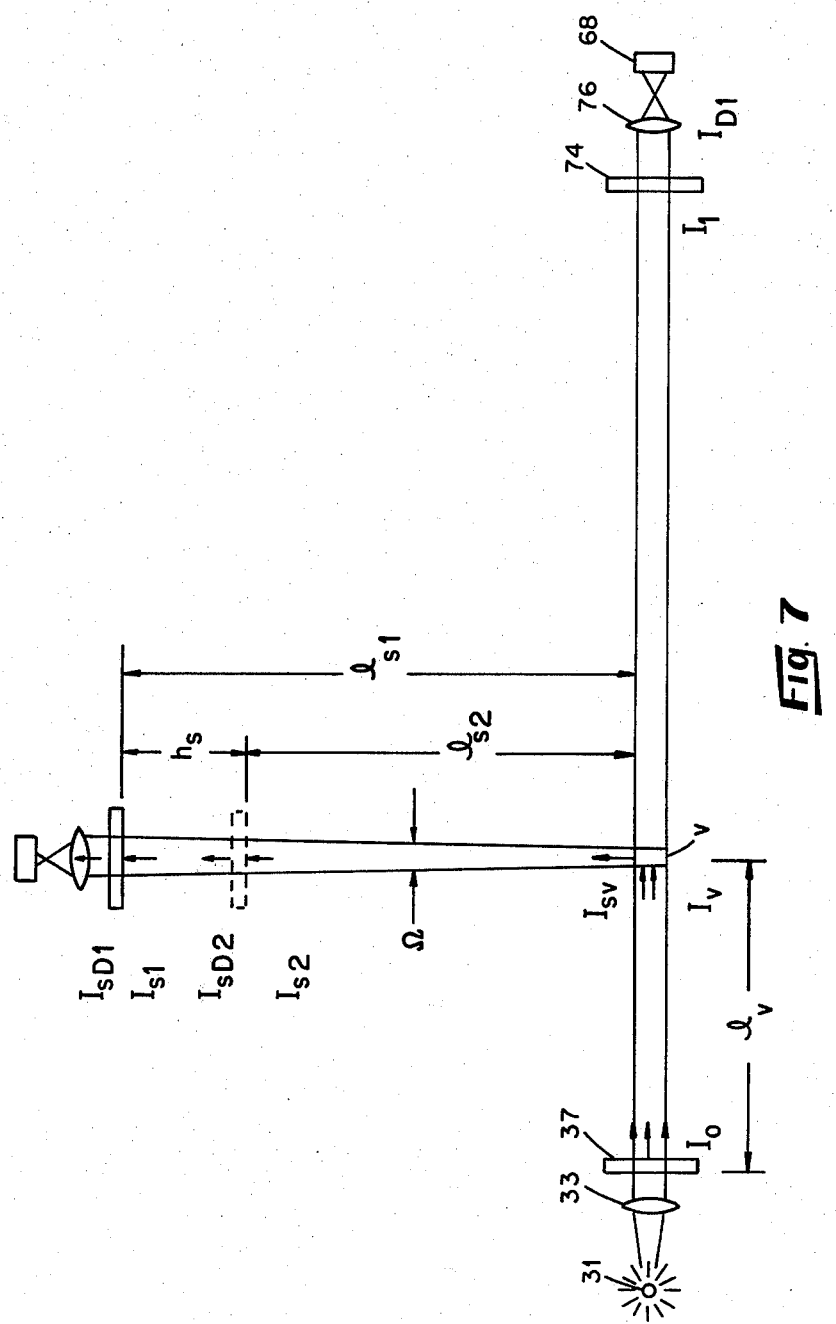
FIG. 7 is a schematic depicting certain concepts associated with determination of light scatter associated with the present invention.

To describe the phenomenon of scattering mathematically, yet in practical terms useful in these considerations, reference is made to FIG. 7. Here the intensity of light incident on the scattering volume v is $I_v$, that scattered from v toward the scattered-light detector is $I_{sv}$, and that incident on the window in front of the scattered-light detector is $I_{s1}$. The relationship between these quantities may be written as follows:

$$I_{sv} = I_v \sigma v \Omega \qquad \text{Eq. (15)}$$

$$I_{s1} = I_{sv} e^{-\alpha_s l_{s1}} \qquad \text{Eq. (16)}$$

where the distances $l_{s1}$ and $l_v$ are as shown in FIG. 7.

Equation (15) describes the scattering process: $I_{sv}$ is the intensity of light scattered and is given by the product of $I_v$, the scattering volume v, the solid angle $\Omega$ of acceptance of the scattered-light detector, and $\sigma$, the fraction of light scattered per unit volume of the sample and per unit solid angle at 90°.

The quantity $\sigma$ contains the scattering properties of the sample and is, therefore, a basic quantity and is the quantity employed in the present invention. In FIG. 7 the sample dimension perpendicular to the primary light beam is shown to be large compared to the beam diameter, and large compared to the scattering volume. In this case, the scattered light may be attenuated and Eq. (16) describes this attenuation. The attenuation coefficient $\alpha_s$ for the 90° scattered light may be different from $\alpha$, that for the primary beam, since the scattered wavelength spectrum may be different from the primary beam spectrum. The quantity $\alpha_s$ can be determined unambiguously by scattered light measurements at two distances $l_{s1}$ and $l_{s2}$; the same principles apply here as in the primary beam attenuation measurement referred to hereinbefore, provided only that the solid angle $\Omega$ remains the same in the two measurements. Then $$s = \frac{1}{l_{s2} - l_{s1}} \ln \frac{I_{s1}}{I_{s2}} \qquad \text{Eq. (17)}$$

Where $I_{s1}$ and $I_{s2}$ are the scattered light intensities incident on the detector for the two detector positions.

The scattered light will not only be attenuated by the fluid but also, by an unknown amount, through the detector window. Furthermore, the incident light intensity in the scattering volume, $I_v$, is not known directly. Both of these unknowns are eliminated, however, by employing the same window/detector combination for the transmission and the scattering measurements. More specifically, the fraction of light lost in the detector window is $w_2$. Thus, the scattered light incident on the detector at a distance $l_{s1}$ from the scattering volume is (see FIG. 7)

$$I_{sD1} = (1-w_2)I_{s1} \qquad \text{Eq. (18)}$$

Combining Eqs. (15) through (18) yields $$I_{sD1} = (1-w_2)I_v \sigma v \Omega e^{-\alpha_s l_{s1}} \qquad \text{Eq. (19)}$$

Applying equations relating to window fouling as set forth above, it is seen that the light intensity $I_{D1}$ measured by the same detector in the transmission measurement is related to the incident light intensity at the scattering volume by $$I_{D1} = I_v(1-w_2)e^{-\alpha(l_1-l_v)} \qquad \text{Eq. (20)}$$

Combining Eq. (19) and (20) results in $$I_{sD1} = I_{D1}e^{\alpha(l_1-l_v)}\sigma v \Omega e^{-\alpha_s l_{s1}} \qquad \text{Eq. (21)}$$

where the window transmission factor $(1-w_2)$ cancels out completely.

Thus, the quantity measured is $\sigma$, the scattering coefficient, and $\sigma$ can be expressed as a function of the constant instrument parameters $l_{s1}$, $l_1$, $l_v$, v and $\Omega$ and the attenuation coefficients $\alpha$ and $\alpha_s$ which have both been determined by two-position measurements.

$$\sigma = \frac{1}{v\Omega} \frac{I_{sD1}}{I_{D1}} e^{-\alpha(l_1-l_v)} \cdot e^{\alpha s l_{s1}} \quad \text{Eq. (22)}$$

Only the actual light intensities at the detector, $I_{sD1}$ and $I_{D1}$, enter in the determination of $\sigma$ and thus the measurement is again independent of window fouling and light source variations as long as these remain substantially constant during a set of measurements.

In accordance with the present method, as in measuring the axial attenuation, the scattered light intensity measurement is made at at least two points separated by a known distance from each other and by a known distance from the scattering volume. In addition, the scattering volume must be known and the acceptance solid angles of the detector must be known at the two positions. These latter two factors, in the disclosed system, are fixed properties of the system.

As noted, distinct advantages are available through the use of the same window/detector combination for both transmittance and scattering measurements. In the present system this is accomplished by reorienting the window/light source element between a position in-line with the detector (180°) and a position perpendicular to the axis of the detector acceptance angle (90°). It will be recognized, of course, that alternatively the detector can be rotated instead of the light source, and, in fact the mathematical derivation provided hereinbefore, and depicted in FIG. 7 shows rotation of the detector.

Figure 2:
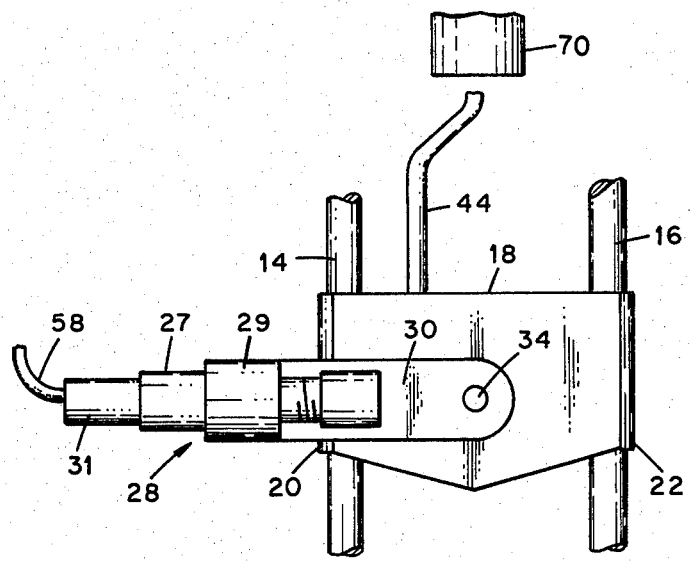
FIG. 2 is a fragmentary representation of the light source portion of the instrument depicted in FIG. 1 but rotated 90 degrees.
Figure 3:
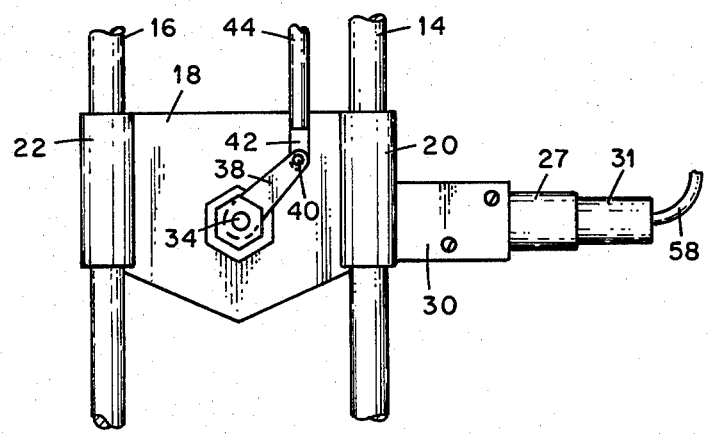
FIG. 3 is a fragmentary representation showing the reverse side of the light source depicted in FIG. 2.

Referring to FIGS. 1-3, there is depicted one embodiment of apparatus for carrying out the method of the present invention. Referring specifically to FIG. 1, the depicted apparatus comprises a cap mounting plate 10 adapted to fit over a container (not shown) for a quantity of material to be sampled or mounted on the end of a pipe or the like for insertion into an open body of water. A pair of rigid mounting rods 14 and 16 are secured at respective ones of their ends 18 and 20 in the plate 10 and depend therefrom as shown in FIG. 1. A mounting plate 18 is adjustably supported on the rods 14 and 16 as by sleeve members 20 and 22 that are slidably received on the rods 14 and 16. Set screws 24 and 26 are provided to secure the mounting plate 18 in a fixed position along the length of the rods 14 and 16. As best seen in FIG. 1, there is mounted in the approximate center of the mounting plate 18 a light source indicated generally by the numeral 28. The depicted light source comprises a tubular housing 27 that is held in a collar 29 that is in turn secured to a mounting bracket 30. Within the housing 27 there is mounted an incandescent lamp 31 and a focusing optics system 33 (see FIG. 4) such that a substantially collimated broad spectrum (e.g., white light) beam of light is projected from the housing 27 out of its end 35 along a path that is substantially coaxial with the longitudinal axis of the housing 27. A transparent window 37 closes the end 35 of the housing 37.

The mounting bracket 30 has one of its ends 32 fixed to a shaft 34 that extends through the thickness of the mounting plate 18 and which is rotatable with respect to the plate 18. As seen in FIG. 3, the opposite end of this shaft 34 projects outwardly from the opposite side of the plate 18 to have fixedly secured thereto a bell crank 38. At the outboard end of the bell crank 38, there is provided a shaft 40 which pivotally secures to the end of the bell crank, the end 42 of a rigid rod 44. This rod 44 extends toward the cap 10 (see FIG. 1) and is slidably received through the thickness thereof to be connected by a shaft coupling 46 to a stepping motor 48. Electrical leads 49 connect the motor 48 to a multiple-pin electrical connector 51 of conventional design. It will immediately be seen that operation of the stepping motor 48, functioning through its shaft 50 which is in turn coupled to the rod 46, serves to move the rod 46 back and forth along its longitudinal axis as indicated by the arrow A in FIG. 1, thereby acting through the bell crank 38 and shaft 34 to rotate the light source mounting plate 30. In the depicted embodiment, this degree of rotation is between a position of alignment of the beam of light from the light source with the central axis of the solid acceptance cone of a detector assembly 66 to be referred to hereinafter (as shown in FIG. 1), and a second position wherein the beam of light is aligned at an angle of 90° with respect to the detector axis as depicted in FIG. 2.

Figure 4:
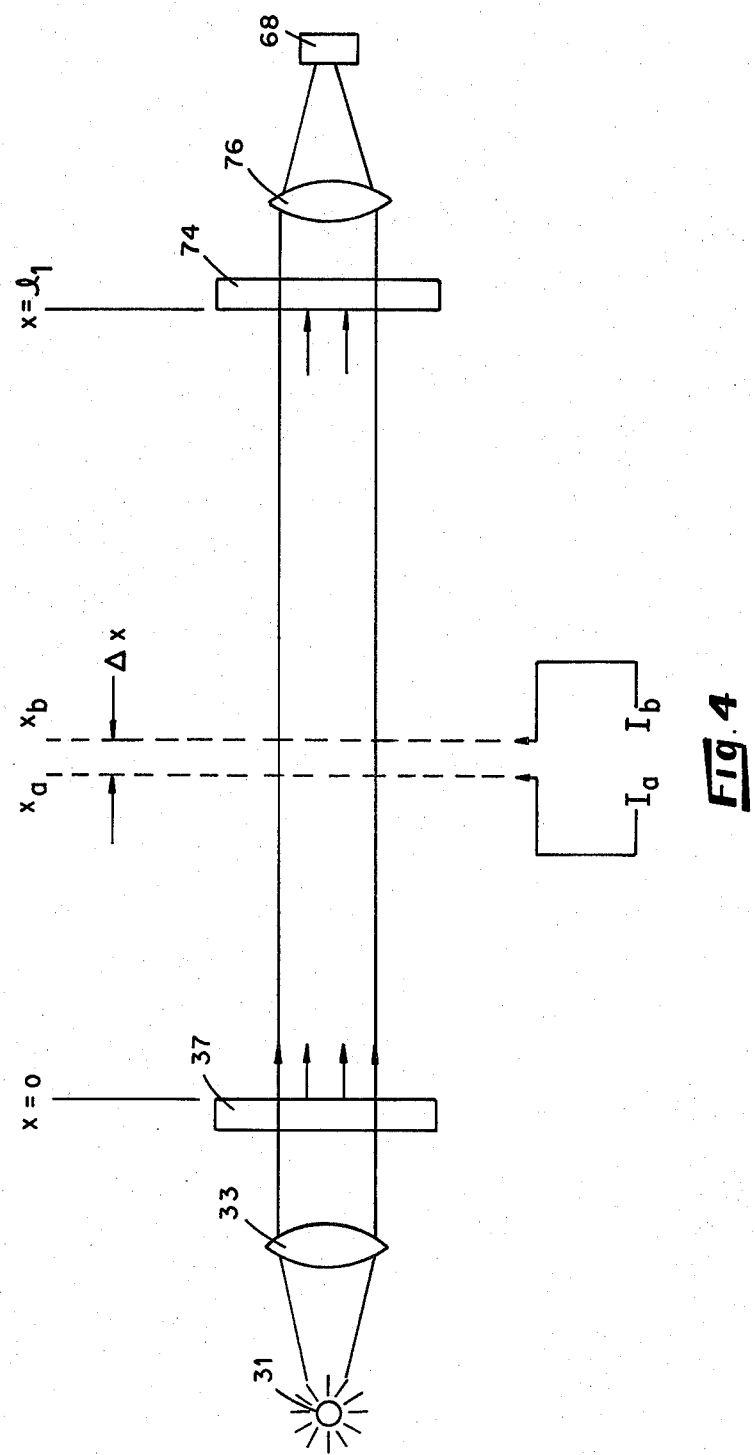
FIG. 4 is a schematic depicting certain concepts of light transmittance associated with the present invention.

The depicted apparatus further includes a detector assembly 66 including a photodetector 68 (see FIG. 4) of conventional design that is capable of detecting light and developing an electrical signal that is representative of the intensity of such detected light. This detector 68 is contained in a hollow cylindrical housing 70 the outboard end 72 of which is closed by a window 74 and which contains focusing optics 76 (FIG. 4). The opposite end 78 of the housing 70 is secured, as by a coupling sleeve 80 to one end 81 of a rigid rod 82 that is slidably received in an opening 84 through the thickness of the cap 10. The opposite end 86 of the rod 82 is provided with an elongated, internally threaded coupling 90 which includes a rigid arm 92 extending generally perpendicularly therefrom and has its distal end 94 slidably received in a slot 96 defined in the wall 98 of a mounting bracket 100. By this arrangement the coupling is maintained against rotation while enjoying longitudinal freedom of movement. This coupling 90 is threadably received on the threaded shaft 102 of a stepping motor 104 that is mounted in the bracket 100. Accordingly, when the stepping motor is activated, its shaft 102 rotates within the coupling 90 which is held against rotation by the arm 92 so that the resultant movement of the detector assembly 66 is linear along a path coaxial with the longitudinal axis of the detector housing 70 as indicated by the arrow B in FIG. 1. It is noted that the motor 104 is rotationally bidirectional to provided for reciprocatory movement of the detector assembly 70 by measurable amounts. Electrical leads 106 extend from the motor 104 to the connector 51.

Figure 8:
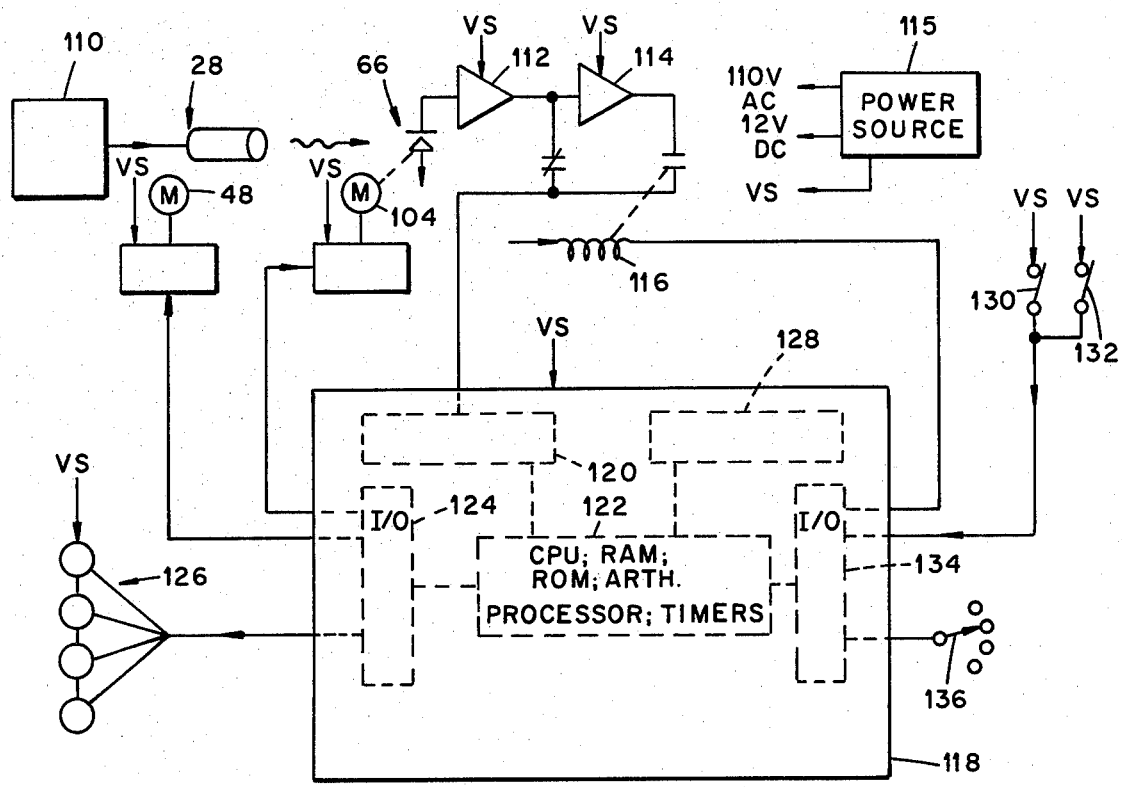
FIG. 8 is a schematic depicting one embodiment of a control system employed in conjunction with the device depicted in FIG. 1.

With reference to FIG. 8, one suitable control system for the depicted apparatus includes a power source 115 which provides 110 volts A.C., 12 volts D.C., and one or more lower voltages which are supplied to the control system at appropriate locations, vs, within the system. In the depicted control system, the light source 28 is powered through a regulated power source 110 to provide substantially constant voltage to the lamp 31. When the light beam is detected at the photodetector assembly 66 the electrical signal developed by the photodetector is fed to one of two amplifiers 112 and 114 where the signal is amplified. Such amplified signal is fed to a micro-computer 118 which in the depicted system includes an analog-to-digital converter 120 that initially receives the amplified detector signal and feeds its digital output signal to a central processing unit 122 that comprises a read only memory, random access memory, arithmetic processor, and various timers. Appropriate electrical signals from the central processing unit and/or its components are fed through an input- /output unit 124 to the stepping motors 48 and 104 and/or to other functions such as linear position indicators 126. Appropriate ones of the output signals from the central processing unit are also fed to a display 128. Electrical power for the central processing unit and its components is fed thereto from the voltage source 115 through switches 130 and 132 and an input/output unit 134. As depicted, a display select switch 136 is provided to select the parameter to be displayed, e.g., percent transmission, percent scatter, etc. The amplifier 112 is employed when making a light transmission measurement and the amplifier 114 is employed when making a light scatter measurement. Automatic selection for the amplifiers 112 and 114 is provided for through a relay 116 connected through the input/output unit 134 to the central processing unit. Each of the components of the depicted system are commercially available and their individual functions are well understood by one skilled in the art.

In a typical operation of the depicted apparatus for measuring the "turbidity" of a particulate-containing liquid medium, the light source 28 and the detector 66 are immersed beneath the surface of a quantity of the liquid medium. This quantity may be contained in a vessel as a "grab" sample or it may be an open body of water. It is important that the liquid not flow past the windows of the light source and detector in a manner which washes the windows between measurements. Fouling of the windows, per se, does not affect the measurements in that the contribution of fouled windows is cancelled out as noted hereinbefore. Stability of the sample is necessary for only the relatively short time, e.g., a fraction of a minute, required for a series of measurements.

Power is next applied to the device whereupon the light source directs a beam of light through the medium toward the detector, which in a preferred embodiment is in-line with the beam axis. The detector thereupon generates a first electrical signal which is representative of the intensity of the detected light. This signal is amplified and fed to the central processing unit (CPU) and stored, along with the linear position of the detector along the length of the rods 14 and 16 as determined from the position of the shaft 102 of the stepping motor 104, hence the linear distance between the light source and the detector. The CPU next supplies a signal to the stepping motor 48 to rotate the light source by 90 degrees, whereupon the detector again is caused to detect the intensity of the scattered light at this angle and develop a second signal that is representative of the intensity of the detected scattered light. This signal is amplified and fed to the CPU. In the present device, the light source is next returned to its in-line position upon actuation of the stepping motor in reverse by a signal from the CPU. Thereafter, or simultaneously, a signal is fed from the CPU to the stepping motor 104 to move the detector away from the light source by a preselected distance which is stored in the CPU. When the detector is at its new location, it detects the intensity of the light transmitted thereto from the light source along the now-extended path and develops a third electrical signal that is representative of such detected intensity. This signal is amplified and fed to the CPU. Thereupon, a signal is fed to the stepping motor 48 to rotate the light source 90 degrees whereupon the detector is caused to detect the scattered light at the new position and develop a fourth electrical signal that is representative of the detected scattered light. This fourth signal is amplified and fed to the CPU.

Within the CPU, the first and third electrical signals are compared and their difference is displayed as the percent transmittance of the sample. Further, the second and fourth signals are compared and their difference is displayed as the percent scatter of the medium. Employing Eq. 9, the CPU further calculates the transmittance coefficient, $\alpha$, of the medium and supplies the same for display. In like manner, the scatter coefficient is calculated, using Eq. 16 and is made available for display.

Notably, in the present system there is no absolute calibration required inasmuch as the system employs a ratio of measurements at the different path lengths. As desired, calibration of relative intensities may be carried out employing a set of standard gratings or the like to provide a number of points corresponding to various liquid opacities.

The stability of the source and detector, as well as window coatings, can be easily checked together, simply by occasionally repeating a transmittance measurement at the first location. If this further measurement agrees with the first, the entire system has remained stable in all respects.

The determinations made by the present system have been found to be both accurate and precise. They are quickly made, even under a variety of use conditions. The system is highly portable and can readily be converted between manual or automatic operation, and/or between simple sample determinations or multiple sample determinations over an extended period of time.

While a preferred embodiment has been shown and described, it will be understood that there is no intent to limit the invention by such disclosure, but rather, it is intended to cover all modifications and alternate constructions falling within the spirit and scope of the invention as defined in the appended claims.

What is claimed:

1. A method for measuring light transmittance and scatter in a liquid medium comprising the steps of directing a substantially collimated beam of relatively broad spectrum light into said medium from a source of said light, detecting the light intensity at a first axial location along the length of said beam, converting said detected light intensity to a first electrical signal, changing the relative angular positions of said beam and said detector to a first angular position wherein the axis of said beam is oriented at an angle with respect to said detector such that the projected solid acceptance angle of said detector intersects said beam to define a first sampling volume at a first sampling position along the length of said beam, detecting the light intensity in said first sampling volume employing said detector, converting said last mentioned detected light intensity to a second electrical signal that is representative of said light intensity in said first sampling volume, detecting the light intensity at a second axial location along the length of said beam employing the detector as aforesaid, such second axial location being spaced apart along the length of said beam from said first axial location by a known distance, converting said detected light intensity at said second axial position to a third electrical signal that is representative of said detected light intensity at said second axial position, changing the relative angular positions of said beam and said detector to a second angular position wherein the axis of said beam is oriented at an angle with respect to said detector such that the projected solid angle of acceptance of said detector intersects said beam to define a second sampling volume at a second position along the length of said beam, said first and second angular positions being angularly substantially equal, said second position of said second sampling volume being spaced apart along the length of said beam by a known distance, detecting the light intensity in said second sampling volume employing said detector, converting said detected light intensity to a fourth electrical signal that is representative of said light intensity in said second sampling volume, comparing said first and third electrical signals and converting their ratio to an electrical signal that is representative of the axial light transmittance of said medium, and comparing said second and fourth electrical signals and converting their ratio into an electrical signal that is representative of the light scatter in said medium.

2. The method of claim 1 and including the step of displaying said ratio between said first and third signals and said ratio between said second and fourth signals.

3. The method of claim 1 and including the steps of returning said light source and said detector to their respective starting positions, detecting the intensity of light reaching said detector at such last mentioned position, converting said detected light to an electrical signal that is representative of said detected light, and comparing said last mentioned signal to said first signal.

4. Apparatus for measuring light transmittance and scatter in a liquid medium comprising a source of relatively broad spectrum light, means directing a beam of said light into said medium, detector means disposed within said medium and intercepting said beam to develop a first electrical signal that is representative of the intensity of the light that has been transmitted to said detector, means changing the angular relationship of said beam and said detector whereby said detector receives substantially only light scattered from said beam to develop a second electrical signal that is representative of the intensity of scattered light reaching said detector, means changing the linear distance between said light source and said detector by a determined amount whereupon said detector develops a third electrical signal that is representative of the light transmitted thereto at said changed distance and a fourth electrical signal that is representative of the light scattered thereto at said changed linear distance and at the same angular relationship as aforesaid, means electrically determining the ratio of said first and third signals and the ratio of said second and fourth signals.

* * * * *

UNITED STATES PATENT OFFICE
CERTIFICATE OF CORRECTION

Patent No. 4,290,695      Dated September 22, 1981

Inventor(s) HAROLD W. SCHMITT

It is certified that error appears in the above-identified patent and that said Letters Patent are hereby corrected as shown below:

Column 3, line 48, after "by" and before "may" insert -- $\alpha$ -- (lower case Greek letter Alpha)

Column 7, line 16, after "known" insert -- (and preferably held constant) --

Signed and Sealed this

Twelfth Day of January 1982

[SEAL]

Attest:

Attesting Officer

GERALD J. MOSSINGHOFF

Commissioner of Patents and Trademarks